United States Patent

Rocque et al.

(10) Patent No.: US 10,292,623 B2
(45) Date of Patent: May 21, 2019

(54) APPARATUS AND METHOD FOR DETERMINING A RESPIRATION VOLUME SIGNAL FROM IMAGE DATA

(71) Applicant: KONINKLIJKE PHILIPS N.V., Eindhoven (NL)

(72) Inventors: Mukul Julius Rocque, Eindhoven (NL); Caifeng Shan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 277 days.

(21) Appl. No.: 14/772,427

(22) PCT Filed: Mar. 12, 2014

(86) PCT No.: PCT/IB2014/059663
§ 371 (c)(1),
(2) Date: Sep. 3, 2015

(87) PCT Pub. No.: WO2014/141085
PCT Pub. Date: Sep. 18, 2014

(65) Prior Publication Data
US 2016/0007883 A1   Jan. 14, 2016

Related U.S. Application Data

(60) Provisional application No. 61/789,206, filed on Mar. 15, 2013.

(30) Foreign Application Priority Data

Mar. 15, 2013   (EP) ..................................... 13159416

(51) Int. Cl.
*A61B 5/091*   (2006.01)
*A61B 5/087*   (2006.01)
(Continued)

(52) U.S. Cl.
CPC ............ *A61B 5/091* (2013.01); *A61B 5/0075* (2013.01); *A61B 5/0077* (2013.01); *A61B 5/087* (2013.01);
(Continued)

(58) Field of Classification Search
CPC ........ A61B 2560/0223; A61B 2576/00; A61B 5/0075; A61B 5/0077; A61B 5/0816;
(Continued)

(56) References Cited

U.S. PATENT DOCUMENTS

| 4,373,534 A | 2/1983 | Watson |
| 5,800,360 A | 9/1998 | Kisner et al. |

(Continued)

FOREIGN PATENT DOCUMENTS

| JP | 2005246033 | 9/2005 |
| WO | 2009036312 A1 | 3/2009 |

(Continued)

OTHER PUBLICATIONS

BTS Bioengineering; BTS OEPSYSTEM; Opto-Electronic System for Pulmonary Ventilation Measurement; obtained from the internet: www.btsbioengineering.com/products/kinematics/btsoepsystem recovered Jun. 6, 2015.

(Continued)

*Primary Examiner* — Mark D Remaly

(57) ABSTRACT

The present invention relates to apparatus (10) for determining a respiration volume signal from a subject (12), comprising a processing unit (28) for receiving image data (26) detected from a field of view (42) and for determining an alternating signal (S) including vital sign information (R) of the subject (12) from the image data (26), an analysis unit (30) for determining at least one characteristic parameter (A) corresponding to a respiration parameter of the subject (12) on the basis of the alternating signal (S), a calibration unit (Continued)

(32) for determining a calibration value (V1, V2) on the basis of a breathing volume measured during inhale and/or exhale of the subject (12) by means of an airflow or an air volume measurement, and a calculation unit (34) for calculating the respiration volume of the subject (12) on the basis of the calibration value (V1, V2) and the at least one characteristic parameter (A).

19 Claims, 6 Drawing Sheets

(51) Int. Cl.
    *A61B 5/11* (2006.01)
    *A61B 5/113* (2006.01)
    *A61B 5/00* (2006.01)
    *A61B 5/08* (2006.01)

(52) U.S. Cl.
    CPC .......... *A61B 5/0816* (2013.01); *A61B 5/0873* (2013.01); *A61B 5/1128* (2013.01); *A61B 5/1135* (2013.01); *A61B 5/7246* (2013.01); *A61B 5/7278* (2013.01); *A61B 2560/0223* (2013.01); *A61B 2576/00* (2013.01)

(58) Field of Classification Search
    CPC ....... A61B 5/087; A61B 5/0873; A61B 5/091; A61B 5/1128; A61B 5/1135; A61B 5/7246; A61B 5/7278
    See application file for complete search history.

(56) References Cited

U.S. PATENT DOCUMENTS

| | | |
|---|---|---|
| 2004/0254492 A1 | 12/2004 | Zhang et al. |
| 2008/0243019 A1 | 10/2008 | Tsujimura |
| 2010/0324437 A1 | 12/2010 | Freeman et al. |
| 2011/0251493 A1 | 10/2011 | Poh et al. |
| 2012/0289850 A1 | 11/2012 | Xu et al. |
| 2013/0002832 A1 | 1/2013 | Lasenby et al. |
| 2014/0037166 A1 | 2/2014 | De Haan et al. |
| 2014/0243649 A1 | 8/2014 | Rocque et al. |

FOREIGN PATENT DOCUMENTS

| | | |
|---|---|---|
| WO | 2011127487 A2 | 10/2011 |
| WO | 2012140531 A1 | 10/2012 |

OTHER PUBLICATIONS

Chen, H., et al.; Color structured light system of chest wall motion measurement for respiratory volume evaluation; 2010; Journal of Biomedical Optics; 15(2)026013.

Lodovico, A., et al.; Projected Light System for Trunk Surface Reconstruction and Volume Measurement During Respiration; 2010; ISBS; vol. 1:pp. 1-2.

Peacock, A. J., et al.; Optical mapping of the thoracoabdominal wall; 1984; Thorax; 39:93-100.

Peacock, A., et al.; Optical measurement of the change in trunk volume with breathing; 1985; Bulletin Europeen de Physiopathologie Respiratoire; 21(2)125-129.

Penne, J., et al.; Robust Real-Time 3D Respiratory Motion Detection Using Time-of-Flight Cameras; 2008; Int. Journal of Computer Assisted Radiology and Surgery; 3(5)427-431.

Yu, M-C., et al.; Noncontact respiratory measurement of volume change using depth camera; 2012; Int. Conf. of IEEE Engineering in Medicine and Biology Society; pp. 2371-2374.

APPARATUS AND METHOD FOR DETERMINING A RESPIRATION VOLUME SIGNAL FROM IMAGE DATA

CROSS REFERENCE TO RELATED APPLICATIONS

This application is a national filing of PCT application Ser. No. PCT/IB2014/059663, filed Mar. 12, 2014, published as WO 2014/141085 A1 on Sep. 18, 2014, which claims the benefit of U.S. provisional application Ser. No. 61/789,206 filed Mar. 15, 2013 and EP provisional application serial no. 13159416.0 filed Mar. 15, 2013, both of which are incorporated herein by reference.

FIELD OF THE INVENTION

The present invention relates to an apparatus for determining a respiration volume signal from a subject and a corresponding method, in particular, the present invention relates to measurements which can be used for remotely determining the respiration volume of a subject, wherein the region of interest is automatically determined and the respiration volume of the subject is determined frequently or continuously by a remote measurement.

BACKGROUND OF THE INVENTION

Vital signs of a person, for example the respiration rate serve as indicators for the current state of the person and as predictions of serious medical events. For this reasons, vital signs are extensively monitored in in-patient and out-patient care settings, at home or in further health, leisure or fitness settings.

Camera-based monitoring of the vital signs or physiological signals such as respiratory rate is a known technique for remotely or contactless measuring the vital signs of a person. The camera-based monitoring of vital signs allows apart from the advantage of being fully contactless, two-dimensional information, which enables a multi-spot and large area measurement, and often contains additional context information. This additional information can be used in the measurement of additional vital signs such as respiratory volume.

The respiratory volume measurement is important for respiratory disease diagnosis and therapy evaluation such as sleeping diagnosis and neonatology. Common systems for measuring a respiratory volume in clinical practice require the use of spirometers, however these spirometers are bulky, require a lot of probes and are flow-based measurements, which force the subject to breathe in and breathe out of a tube, which is extremely inconvenient for the user. The measurement is further highly dependent on the patient's cooperation and it interferes with the subject's normal respiration and the use is difficult for patients with breathing difficulties.

Existing camera-based respiration volume measurements require either the computation of a three-dimensional map of the entire thorax or need markers which are attached to the subject. The three-dimensional surface reconstruction requires an accurate estimation of the entire thorax by the camera and needs an active radiation source or multiple cameras to provide a reliable three-dimensional map which is a large technical effort. Alternatively, the use of markers, which have to be attached to the thorax of the subject is inconvenient in practice.

A corresponding apparatus for measuring the respiration variability using impedance contact probes for measuring the body movement is for example known from WO 2009 363 12 A2.

Other methods are known using depths-sensing cameras or three-dimensional cameras to detect the respiration and to determine the respiration volume of a subject.

The disadvantage of the known methods to measure the respiratory volume from a subject is that the technical effort is increased due to the complicated three-dimensional optical measurement of the respiration volume or that the use of the known systems is inconvenient due to the use of spirometers or markers for the detection of the motion of the subject's thorax.

SUMMARY OF THE INVENTION

It is an object of the present invention to provide an improved apparatus and a corresponding improved method for determining a respiration volume signal from a subject which is more convenient for the user and can be implemented with low technical effort.

According to one aspect of the present invention, an apparatus for determining a respiration volume signal from a subject is provided comprising:

a processing unit for receiving image data determined from a field of view and for determining an alternating signal including vital sign information of the subject from the received image data, an analysis unit for determining at least one characteristic parameter corresponding to a respiration parameter of the subject on the basis of the alternating signal, a calibration unit for determining a calibration value on the basis of a breathing volume measured during inhale and/or exhale of the subject by means of an airflow or an air volume measurement, and a calculation unit for calculating the respiration volume of the subject on the basis of the calibration value and the at least one characteristic parameter.

According to another aspect of the present invention, a method for determining a respiration volume signal from a subject is provided, comprising the steps of:

receiving image data determined from a field of view, determining an alternating signal including vital sign information of the subject from the received image data, determining at least one characteristic parameter corresponding to a respiration parameter of the subject on the basis of the alternating signal, determining a calibration value on the basis of a breathing volume measured during inhale and/or exhale of the subject by means of an airflow or an air volume measurement and calculating the respiration volume of the subject on the basis of the calibration value and the characteristic parameter.

In yet further aspects of the present invention, there is provided a computer program which comprises program code means for causing a computer to perform the steps of the processing method when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method has similar and/or identical preferred embodiments as the claimed device and as defined in the dependent claims.

The present invention is based on the idea to determine an alternating signal by means of a remote measurement on the basis of image data determined from a field of view and to calibrate the measurement by means of an airflow or air volume measurement and to correlate the two measurements in order to calculate the absolute respiration volume of the subject on the basis of the remote measurement. Since the remote measurement is calibrated by means of an airflow or air volume measurement, the remote measurement can be used for determining the absolute respiration volume so that a continuous or frequent remote measurement of the respiration volume is possible without the need of additional markers or a three-dimensional measurement of the subject.

Hence, a remote measurement of the respiration volume of a subject can be provided with low technical effort which is convenient for the user.

In a preferred embodiment, the processing unit is connected to an image detection unit for providing the image data from the field of view. This is a simple possibility to determine the respiration information from the subject contactless with low technical effort.

In a preferred embodiment, the alternating signal is determined on the basis of movement pattern derived from the image data. This is a reliable possibility to determine the respiration information from the subject since the detected movement of the subject has a correspondence with the respiration rate.

According to a preferred embodiment, the alternating signal is determined on the basis of movement vectors determined from the movement pattern. This is a simple solution to determine the alternating signals corresponding to the respiration of the subject with high precision and low technical effort.

According to a preferred embodiment, the processing unit comprises a selection unit for selecting at least one area in the field of view on the basis of a plurality of alternating signals determined from the field of view. This is a simple solution to determine a region of interest from the field of view on the basis of the movement of the subject in the field of view in order to increase the reliability of the measurement and to reduce the probability of incorrect measurements.

It is preferred if the analysis unit is adapted to determine a spectral parameter of the alternating signals for selecting the at least one area. This is a possibility to increase the reliability, since the spectrum of alternating signal is used to select the region of interest such that disturbing signals and noise are not considered for the selection of the region of interest.

According to a further preferred embodiment, the analysis unit is adapted to determine the characteristic parameter on the basis of the alternating signal determined from the selected area. This is a possibility to further increase the reliability of the detection of the respiration signal since the alternating signal is determined from the selected area as the region of interest.

It is further preferred if the at least one characteristic parameter is determined on the basis of a plurality of alternating signals determined from different areas of the field of view. This is a possibility to increase the reliability of the determination of the characteristic parameter since the signal strength of the vital sign can be increased and the noise can be reduced.

It is preferred if the alternating signals determined from the different areas are weighted by a weight factor. This is a possibility to consider the alternating signals from different areas differently on the basis of the signal quality.

It is further preferred if the characteristic parameter is an amplitude of the alternating signal. This is a possibility to correlate the movement of the subject corresponding to the respiration with the respiration volume measured by the calibration unit in order to determine the absolute respiration volume continuously after the initial calibration.

It is further preferred if the calibration unit is adapted to measure the breathing volume of the subject during an inhale or an exhale cycle. This is a possibility to determine the whole breathing volume between a complete exhale and a complete inhale of the subject.

It is further preferred if the calibration unit comprises an airflow measurement device for measuring the breathing volume. This is a simple possibility to calibrate the measurement with low technical effort, since a spirometer on the basis of an airflow measurement can determine the air volume precisely with low technical effort.

In a preferred embodiment, the calibration unit is adapted to correlate the characteristic parameter and the measured breathing volume to determine the calibration value and to calculate the respiration volume. This is a precise possibility to combine the two measurements of the respiration of the subject and to determine the calibration value in order to provide a continuous breathing volume measurement.

In a preferred embodiment, the calibration unit is adapted to measure the breathing volume of the subject during an inhale and an exhale cycle, wherein a maximum inhale volume is correlated to the corresponding maximum of the characteristic parameter and a minimum inhale volume is correlated to the corresponding minimum of the characteristic parameter to determine the calibration value and wherein the characteristic parameter is scaled according to the determined calibration value to continuously calculate the respiration volume. This is a possibility to correlate the two different measurements with low technical effort in order to determine the respiration volume remotely after calibration.

In a preferred embodiment, the calculation unit is adapted to calculate the respiration volume for the respiration cycles following the determination of the calibration value. This is a simple possibility to determine the respiration volume entirely contactless after the calibration has been performed once at the beginning of the measurement.

As mentioned above, the present invention is based upon the idea to determine the respiration volume on the basis of two different measurements. One measurement is based on an airflow in order to calibrate the measurement and the second measurement is a contactless measurement on the basis of received radiation from the subject, wherein the two measurements are correlated in order to determine frequently and/or continuously the respiration volume of the subject on the basis of the remote measurement. Since the results of the two different measurements are used by the apparatus and correlated by apparatus, the respiration volume can be determined with low technical effort and with a high comfort for the patient.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
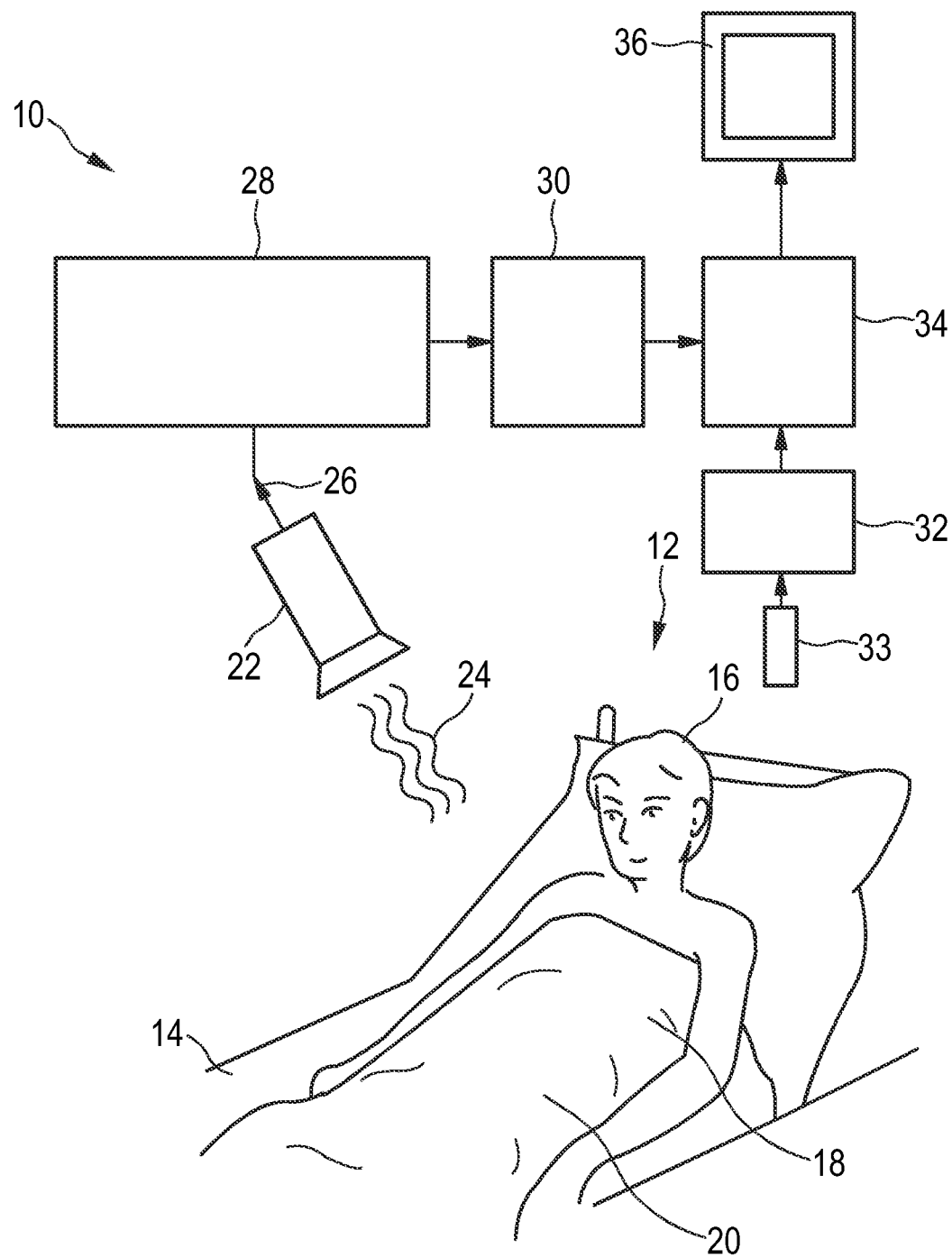
FIG. 1 shows a schematic illustration of a general layout of an apparatus for determining a respiration volume signal from a subject.

FIG. 1 shows a schematic drawing of an apparatus generally denoted by 10 for determining a respiration volume signal from a subject 12. The subject 12, e.g. a patient staying in bed, is resting on a support 14. The subject's head 16 is usually a non-indicative portion regarding the respiration of the subject, wherein the chest 18 is an indicative portion regarding the respiration of the subject 12. The general problem of the common situation shown in FIG. 1 is that the respiration volume cannot be measured remotely or contactless with low technical effort. Usually merely the respiration rate or the heart rate are detected by means of camera systems or remote systems in general.

The apparatus 10 comprises an image detection device 22, e.g. a monochromatic camera which can be used for recording image frames of the subject 12. The image frames can be derived from electromagnetic radiation 24 emitted or reflected by the subject 12. For extracting the image information from the image data 26, e.g. a sequence of image frames, the image data 26 is provided to an image processing unit 28. The monochromatic camera 22 provides a two-dimensional image or image data 26 to the image processing unit 28.

The image detection device 22 is adapted to capture images belonging to at least a spectral component of the electromagnetic radiation 24. The image detection device 22 may provide continuous image data or a discrete sequence of image frames captured from a field of view including the subject 12 to be measured.

The image processing unit 28 is adapted to receive the image data 26 from the image detection device 22, to evaluate the image data 26 in general and to detect a region of interest of the subject 12, i.e. the thorax 18 as indicative portion of the respiration of the subject 12. In order to detect the region of interest, e.g. the thorax 18, the image processing unit 28 is adapted to divide the captured images in sections or areas of the field of the field of view and to evaluate the image sections separately in order to determine the region of interest. The image processing unit 28 divides the captured images into the image sections and detects motion vectors from the different sections corresponding to the motion of the object in the field of view including the motion of the chest 18 or the thorax region 18 of the subject 12 as indicative portion of the respiration. The motion vectors are determined by means of pattern detection in the image sections or by means of edge detection in the image sections. A method for edge or pattern detection and for deriving the motion vectors from the captured image frames is for example disclosed by WO 2012/140531 A1.

The image processing unit 28 determines alternating signals from the motion vectors and determines a spectral parameter of each of the alternating signals by means of a frequency analysis unit comprised in the image processing unit 28 as described in detail in the following. The spectral parameter of each of the sections of the image data 26 are analyzed by a selection unit which is part of the image processing unit 28. The selection unit selects those sections of the image data from which an alternating signal is derived which is supposed to correspond to a respiration signal. The selection unit selects the sections on the basis of the respective spectral parameter. The spectral parameter is a frequency spectrum or a spectral energy distribution of the alternating signal. Since the respiration signal of the subject 12 has a characteristic spectral energy distribution or a characteristic frequency, the selection unit can select the section which comprise the respiration signal of the subject 12 and, therefore the selection unit 10 identifies the chest 18 or the thorax region 18 of the subject 12 in the image data 26 for determining the respiration signal.

The selection unit determines a weight factor for each of the different image sections dependent on the frequency analysis as described in the following.

The image processing unit 28 is connected to an analysis unit 30 and provides the alternating signal to the analysis unit 30 for determining a respiratory signal corresponding to the respiration of the subject 12. The analysis unit 30 receives the alternating signals from the different image sections and the respective weight factors for the different image sections from the image processing unit 28 and calculates the respiratory signal on the basis of the alternating signals and the weight factors. Hence, the respiratory signal is calculated on the basis of the image data 26 and determined entirely contactless. The analysis unit 30 determines at least one characteristic parameter of the respiratory signal, e.g. the amplitude of the respiratory signal and/or the maximum and minimum value of the respiratory signal in order to determine the respiration volume as described in the following.

The apparatus 10 further comprises a calibration unit 32 for calibrating the respiration volume measurement of the apparatus 10. The calibration unit 32 is connected to a spirometer 33, which measures a respiration volume of the subject by measuring an airflow during inhale and exhale of the subject 12. In order to calibrate the apparatus 10 and the respective remote measurement of the respiration, the subject is asked to make a complete exhale and a complete inhale cycle, to detect a respiration signal amplitude for the entire respiration range which is possible for the subject 12. During this complete exhale and inhale cycle, the air volume inhaled and exhaled by the subject 12 is measured by the spirometer 33 while the image detecting device 22 is capturing image data 26 from the subject 12, i.e. from the region of interest determined by the image processing unit 28 and wherein the analysis unit 30 is determining the respiratory signal from the remote measurement. Hence, during the calibration by means of the calibration unit 32 the respiration volume is measured by means of the spirometer 33 and the respiratory signal is determined remotely by means of the image detection device 22, the image processing unit 28 and the analysis unit 30 in order to estimate the absolute respiratory volume for the respiratory signal. The respiratory signal determined by the analysis unit 30 is provided to a calculation unit 34. The measured respiration volume measured by the spirometer 33 is forwarded by means of the calibration unit 32 as a calibration value to the calculation unit 34 in order to correlate the respiratory signal or the characteristic parameter from the remote measurement and the absolute respiratory volume measured by the spirometer 33.

Since at least the maximum and the minimum of the respiratory volume of the subject 12 is measured by means of spirometer 33 and correlated with the respiratory signal or the characteristic parameter from the remote measurement, the absolute respiratory volume can be calculated further on based on the calibration value and the respiratory signal derived from the remote measurement to provide frequently or continuously a measurement of the respiratory volume of the subject 12 without the need of the spirometer measurement. To continuously determine the respiration volume, the amplitude and/or the maximum and minimum value of the respiratory signal is or are linearly scaled and interpolated between the maximum and minimum calibration values of the spirometer measurement. Hence, after calibration, the respiration volume can be calculated on the contactless measurement alone.

The so calculated respiratory volume can be provided to a display 36 to display the measured respiratory volume continuously or frequently.

Hence, after the initial calibration by means of the calibration unit 32 and the spirometer 33, the absolute respiratory volume of the subject 12 can be determined remotely by means of the apparatus 10 in general.

Figure 2:
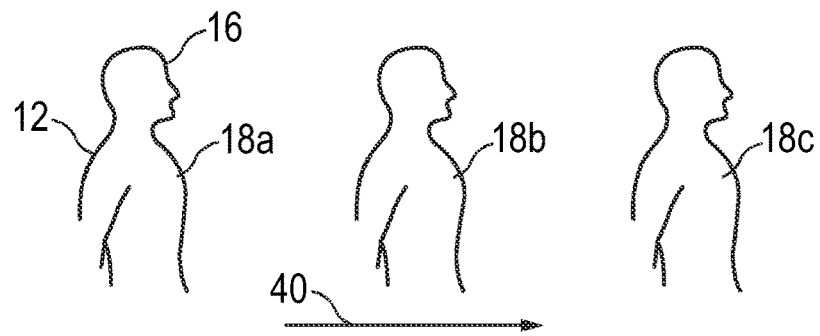
FIG. 2 shows a schematic illustration of a subject's motion indicative of a respiration signal.

FIG. 2 shows a schematic illustration of the subject 12 in order to describe the remote measurement of the respiration of the subject 12. The subject 12 undergoes a characteristic motion of an indicative portion 18 (the chest 18) due to the respiration. When breathing, expansion and contraction of the lung's causes slight motion of characteristic portions of liven beings, e.g. lifting and lowering of the chest 18. Also, abdominal breathing can course characteristic motion of respective parts of the subject's body 12. At least partially periodic motion patterns included by physiological processes can occur in many living beings, particularly in human beings or animals.

Over time, as indicated by an arrow 40, the indicative portion 18 is moved between a contracted position, indicated by reference numerals 18a, 18c, and an extracted portion, indicated by 18b. Essentially, based on this motion pattern, for instance the respiration rate or respiration rate variability can be assessed by means of pattern or edge detection in a captured image sequence. While the indicative portion 18 is pulsating over time, the head 16 as a non-indicative portion remains substantially motionless.

Certainly, also the head 16 undergoes diverse motion over time. However, these motions do not correspond to the periodic pulsation of the chest 18 and can be distinguished by means of the frequency analysis.

Figure 3:
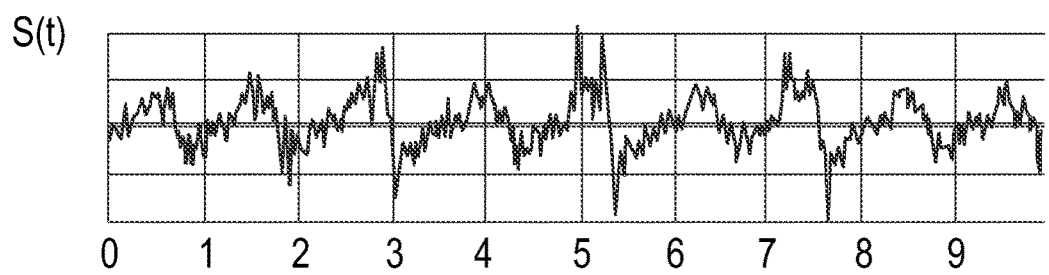
FIG. 3 shows a timing diagram of an alternating signal derived from the subject corresponding to the respiration signal.

FIG. 3 shows a timing diagram of an alternating signal derived from the movement pattern and/or from motion vectors of the different image sections which can be for example determined on the basis of a frame or an edge detection in the respective image section. The alternating signal is generally denoted by $S(t)$. The alternating signal S in this particular case corresponds to the movement of the chest 18 of the subject 12 derived from an image section corresponding to the image data received from the respective indicative portion 18. The alternating signal S shows a characteristic variation corresponding to the movement of the chest 18 i.e. the breathing of the subject 12. The alternating signal S also shows a high-frequency noise superimposed to the breathing.

The alternating signals S are derived from each of the image sections of the field of view wherein a plurality of image sections comprise vital sign information such as a breathing rate and many image sections may comprise disturbing signals which are not related to vital sign information of the subject 12 or other alternating signals which comprise mostly high-frequency noise. In order to identify those image sections from which vital sign information can be derived, the image processing unit 28 comprises the frequency analysis device to perform a frequency analysis of the alternating signals. The frequency analysis is preferably performed by filtering the alternating signals S and/or by performing a Fourier Transformation, in particular a Fast Fourier Transformation (FFT) of the alternating signal S. From the alternating signal, a frequency spectrum is derived in order to identify the image section including vital sign information corresponding to the respiration of the subject 12 as described in the following.

Figure 4:
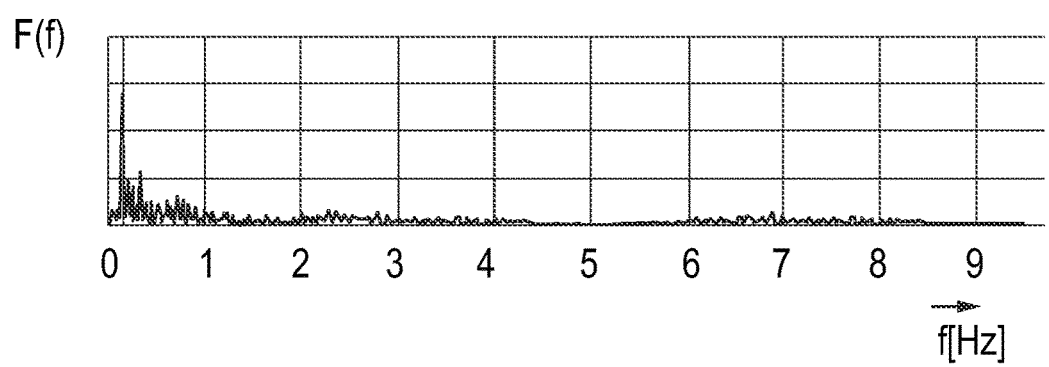
FIG. 4 shows a frequency spectrum of the alternating signal shown in FIG. 3.

FIG. 4 shows a frequency spectrum of the alternating signal S shown in FIG. 3 generally denoted by $F(f)$. The frequency spectrum F shows a large frequency component in a low frequency band, in this particular case between 0 and 1 Hertz, which correspond to the breathing rate of an adult which is normally not higher than 1 Hertz, i.e. 60 breathes per minute. The frequency components higher than a predefined frequency band, e.g. 1 Hertz for adults and 2 Hertz for infants are usually disturbing signals in the image data 26 or correspond to noise of the alternating signal S. In order to characterize the quality of the alternating signal S, the spectral energy of the alternating signal S is determined and an image section is defined as an image section including vital sign information if the spectral energy of the alternating signal S in a predefined frequency band exceeds a predefined threshold level or exceeds a percentage of spectral energy compared to a second frequency band, e.g. the whole frequency spectrum. E.g. if the spectral energy between 0 and 1 or 2 Hertz is larger than a predefined threshold level, e.g. larger than 50% of the entire spectral energy of the alternating signal S or a predefined range of the spectrum, e.g. 2 . . . 3 Hz, 3 . . . 4 Hz, . . . . On the basis of the spectral energy, the image sections are evaluated to select the image sections in the field of view and to determine the region of interest as described in the following.

Figure 5:
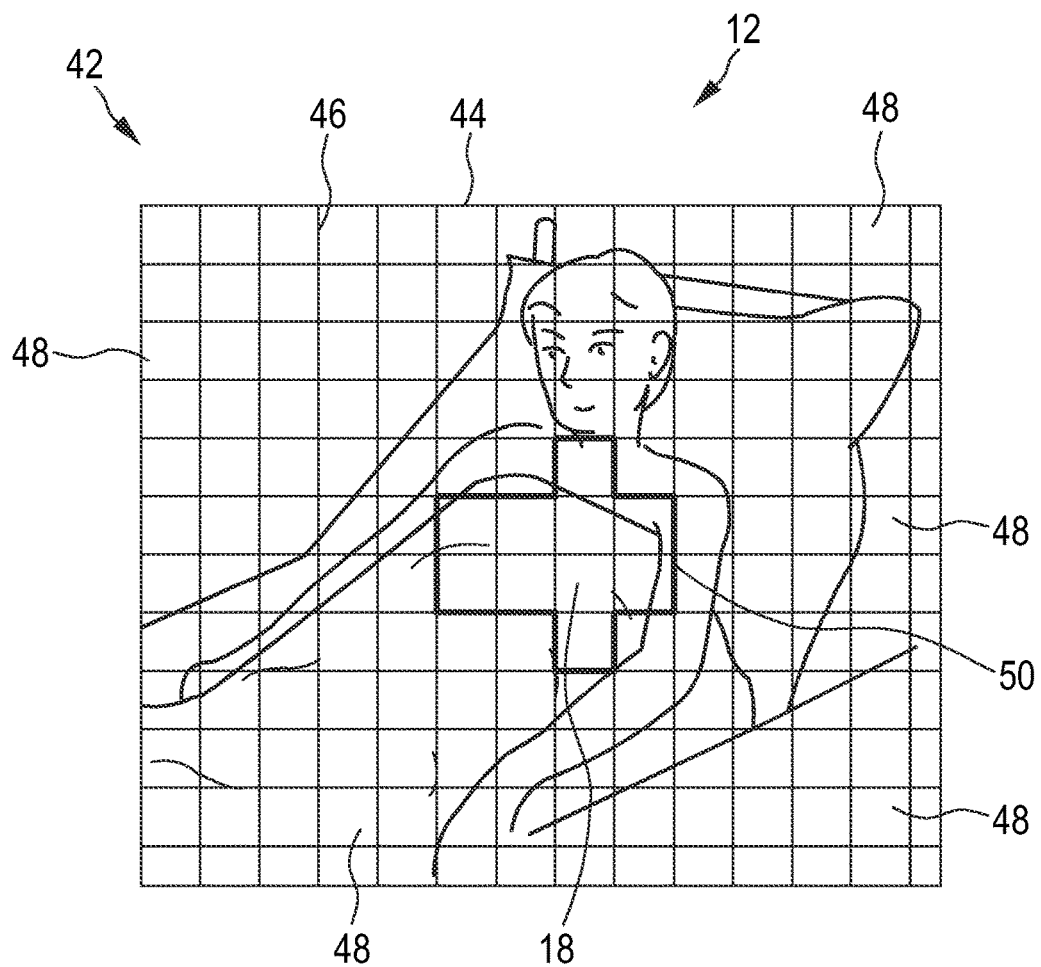
FIG. 5 shows a schematic image for illustrating the selection of a region of interest in the field of view for determining the respiration signal.

FIG. 5 shows a schematic image from a field of view for explaining the detection of the respiratory signal from the subject on the basis of detected image data 26. The field of view detected by the image detection device 22 shown in FIG. 5 is generally denoted by 42. An image frame 44 representing the field of view 42, which is captured by the image detection device 22 shows the subject 12 which is in this case a human being to be measured. In the image frame 44, a grid 46 divides the image frame 44 in different portions and defines image sections 48 to distinguish different areas in the field of view 42 and to determine different motion vectors in the field of view 42. In order to determine the region of interest, i.e. the chest 18 of the subject 12, movement pattern are derived from each of the image sections 48 of the image frame 44 and the alternating signals S are determined from motion vectors determined from the movement pattern of each of the image sections 48 as described above. The motion vectors are determined by pattern detection or edge detection within the different image sections. On the basis of the frequency analysis as described above it is determined whether the movement pattern of the different image sections correspond to a respiratory signal of the subject 12 in the field of view 42 or whether the movement pattern are disturbance signals or noise. The determination whether the movement pattern includes respiratory signals or not is performed as described above on the basis of the spectral parameter and/or the spectral energy and whether the spectral energy is in a frequency band larger than a predefined percentage of the entire spectral energy of the respective alternating signal. On the basis of these data, which are determined for each of the image sections 48, the selection unit selects those image sections which include the respiratory signal and combines those selected image sections 48 to the region of interest, which is in FIG. 5 generally denoted by 50.

On the basis of the alternating signals S which are derived from the image sections 48 of the region of interest 50, the analysis unit 30 determines the respiratory signal. The image processing unit 28 determines a weight factor for each of the selected image sections 48 of the region of interest 50 in order to weight the alternating signals S of the different sections 48 on the basis of the signal quality. The weight factor may be calculated on the basis of the frequency how often the respective image section 48 is selected by the selection unit. In other words, the alternating signals from those image sections 48 which are selected more often as a selected image section 48 are given more weight and the image sections selected less often are given less weight to calculate the respiratory signal. From the different alternating signals, the analysis unit 30 determines the respiratory signal as a single alternating signal.

Figure 6:
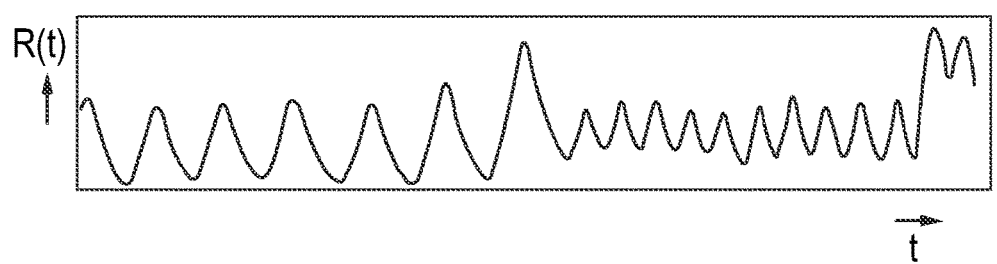
FIG. 6 shows a schematic timing diagram of a respiration signal derived from the image data of the field of view.

FIG. 6 shows a timing diagram of the respiratory signal determined by the analysis unit 30 and generally denoted by R(t). The respiratory signal R(t) is derived from the motion of the chest 18 of the subject 12. From the so determined respiratory signal R, the respiration rate of the subject 12 can be determined. If the calibration values of the calibration unit 32 is correlated with the respiratory signal determined by the analysis unit 30, the absolute respiration volume of the subject 12 can be continuously calculated by the calculation unit 34 as described in the following.

Figure 7:
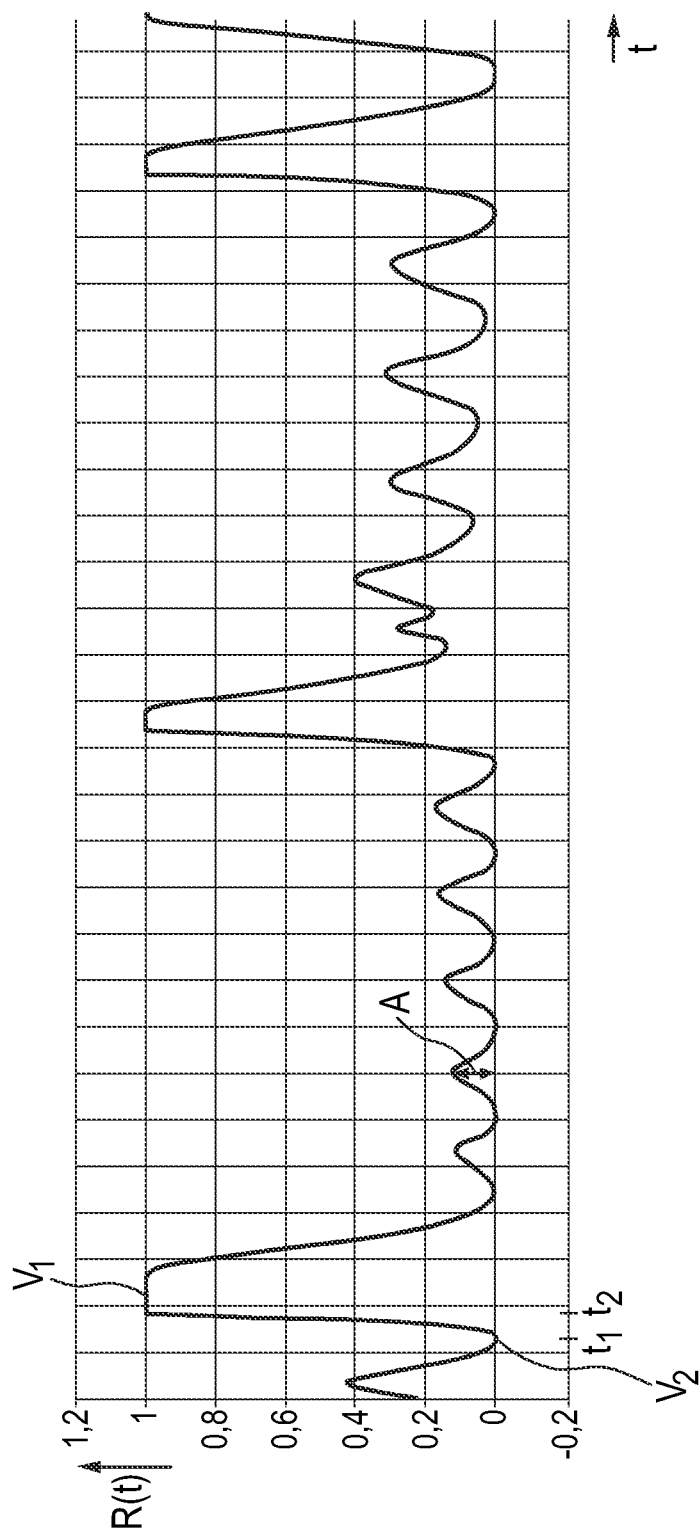
FIG. 7 shows a timing diagram of a respiration signal and the correlation with a calibration measurement of the respiration volume.

FIG. 7 shows a timing diagram of the respiratory signal R(t) during a calibration by means of the calibration unit 32. First, the subject 12 is asked to perform a complete exhale and inhale cycle, wherein the subject 12 first entirely exhales as shown at t1 followed by a complete inhale shown at t2 in order to determine respective calibration values.

An air volume V1 corresponding to the complete exhale at t1, which is for an adult for example 500 ml is measured and defined as 0 volume and the complete inhale air volume V2 which is for an adult for example 3000 ml is measured and defined as 1 as shown in FIG. 7. These measured values V1, V2 of the respiration volume are used as calibration values. The respiration volume V1, V2 between 1 and 0 is linearly scaled so that the amplitude A of the respiratory signal R determined remotely by the analysis unit 30 can be used to calculate the absolute respiratory volume of the subject 12. The scale shown in FIG. 7 can be used together with the entire respiration air volume to determine the absolute respiration volume for each of the following inhale and exhale cycles determined remotely by means of the apparatus 10. Hence, the respiration volume of the subject 12 can be remotely determined continuously or frequently with low technical effort and which is comfortable for the user.

After the calibration has been performed, the subject 12 may move relative to the camera 22 resulting in a change of the alternating signals S received from the thorax 18 as the indicative portion compared to the images used for the calibration. The subject 12 may move perpendicular to the camera viewing direction or may move parallel to the camera viewing direction, i.e. may reduce or increase the distance to the camera 22. In both cases, the movement of the subject 12 has to be detected and considered for the image evaluation and for the determination of the respiratory signal R. For considering the perpendicular movement, certain features in the image like contours or pattern of the subject 12 like clothes or buttons are detected and the movement of the subject 12 can be detected by identifying and following those contours or pattern in the field of view 42. On the basis of the movement of those patterns within the field of view, the region of interest 50 is adapted accordingly so that a recalibration is not necessary after a perpendicular movement of the subject 12. If the subject 12 is moving parallel to the viewing direction of the camera 22, the region of interest 50 has to be scaled in order to determine correct alternating signals and true respiration volume signals from the subject 12. The scaling is performed by contour detection of the subject 12 so that an increase or a decrease of the entire contour size of the subject 12 results in the detection of the movement of the subject 12 parallel to the viewing direction of the camera 22. The measured alternating signals S are scaled accordingly in order to correct the remote measurement.

Hence, a recalibration is not necessary if a subject 12 moves within the field of view 42. A recalibration is only necessary if a subject 12 turns so that the chest 18 as indicative portion is only partially visible by the camera 22.

Figure 8:
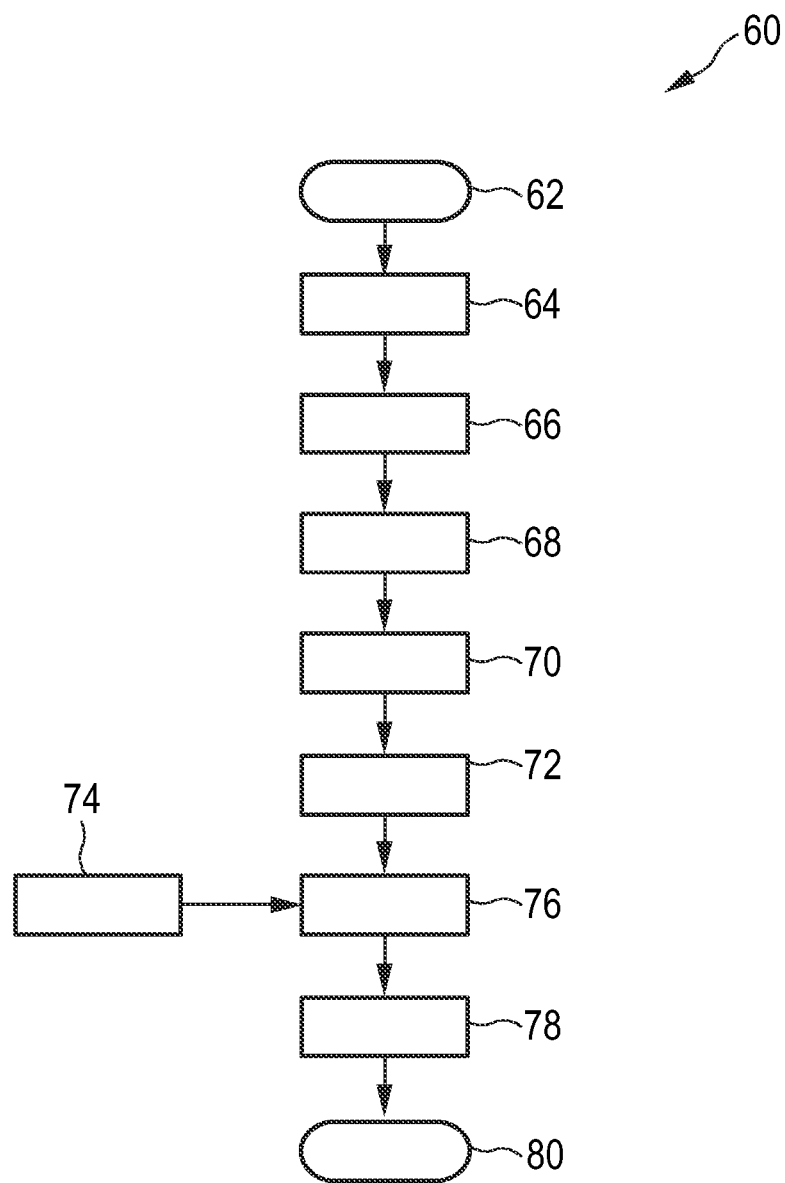
FIG. 8 shows a block diagram representing the steps of an embodiment of a method for determining a respiration volume signal from a subject.

FIG. 8 shows a block diagram illustrating method steps to detect the respiration volume signal from the subject 12. The method is generally denoted by 60. The method 60 starts with step 62. At step 64, an image frame 44 is detected by means of the image detection device 22. At step 66, the image frame 44 or the image data 26 is received by the image processing unit 28 and evaluated by the image processing unit 28 by means of pattern detection or edge detection and the motion vectors are determined for each of the image sections 48 as described above. Depending on the motion vectors, a corresponding alternating signal S is calculated for each of the image sections 48. On the basis of the alternating signals S analyzed by the image processing unit 28 the region of interest 50 is determined at step 68.

At step 70, the analysis unit 30 analyses the alternating signals S. At step 72 the respiratory signal R is determined and the amplitude A of the respiration signal R is calculated.

At step 74, the calibration unit 32 measures the respiration volume of the subject 12 by means of the spirometer 33 and provides the calibration value V1, V2 or a plurality of calibration values V1, V2 to the calculation unit 34. At step 76, the respiration volume is determined on the basis of the calibration value V1, V2 and the respiration signal R. This is usually performed by calculating the amplitude A between a local minimum and a local maximum of the respiration signal R as a characteristic parameter and correlated with the difference between the maximum exhale and the maximum inhale air volume as the calibration values V1, V2 determined by means of the spirometer 33. The local maxima and minima are usually scaled with respect to the calibration values to determine the respiration volume remotely.

At step 78, the respiratory volume is displayed by means of the display 36.

At step 80, the method 60 ends.

Hence, after calibration, the respiration volume can be determined entirely contactless with low technical effort.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for measuring respiration volume of a subject, the apparatus comprising:
   a camera configured to provide image data from a field of view;
   at least one electronic processor programmed to:
   receive the image data from the field of view provided by the camera;
   determine a plurality of alternating signals including vital sign information of the subject from different areas of the field of view from the image data,
   determine at least one characteristic parameter corresponding to a respiration parameter of the subject on the basis of the plurality of alternating signals,
   determine, separately from the at least one characteristic parameter, a calibration value on the basis of a breathing volume measured by a spirometer during at least one of an inhale and exhale of the subject by means of an airflow or an air volume measurement,
   calculate the respiration volume of the subject on the basis of the calibration value and the at least one characteristic parameter wherein the plurality of alternating signals are weighted by a weight factor; and
   control a display device to continuously display the calculated respiration volume of the subject.

2. The apparatus as claimed in claim 1, wherein the plurality of alternating signals are determined on the basis of movement pattern derived from the image data.

3. The apparatus as claimed in claim 1, wherein the at least one electronic processor is further programmed to:
   select at least one area in the field of view on the basis of the plurality of alternating signals determined from the field of view.

4. The apparatus as claimed in claim 3, wherein the at least one electronic processor is further programmed to:
   determine a frequency spectrum or spectral energy distribution of the plurality of alternating signals for selecting the at least one area.

5. The apparatus as claimed in claim 2, wherein the at least one electronic processor is further programmed to:
   determine the characteristic parameter on the basis of the plurality of alternating signals determined from the selected area.

6. The apparatus as claimed in claim 1, wherein the characteristic parameter is an amplitude of the plurality of alternating signals.

7. The apparatus as claimed in claim 1, wherein the at least one electronic processor is further programmed to:
   measure the breathing volume of the subject during at least one of the inhale and the exhale cycle.

8. The apparatus as claimed in claim 1, further comprising:
   a spirometer for measuring the breathing volume.

9. The apparatus as claimed in claim 1, wherein the at least one electronic processor is programmed to correlate the characteristic parameter and the measured breathing volume to determine the calibration value and to calculate the respiration volume.

10. The apparatus as claimed in claim 9, wherein the at least one electronic processor is programmed to measure the breathing volume of the subject during an inhale and an exhale cycle, wherein a maximum inhale volume is correlated to the corresponding maximum of the characteristic parameter and a minimum inhale volume is correlated to the corresponding minimum of the characteristic parameter to determine the calibration value and wherein the characteristic parameter is scaled according to the determined calibration value to continuously calculate the respiration volume.

11. The apparatus as claimed in 1, wherein the wherein the at least one electronic processor is further programmed to:
    calculate the respiration volume for the respiration cycles following the determination of the calibration value.

12. A non-transitory computer readable medium storing instructions executable by at least one electronic processor to perform a method for determining a respiration volume signal from a subject, the method comprising:
    receiving image data detected from a field of view,
    determining a plurality of alternating signals including vital sign information of the subject from different areas of the field of view from the received image data,
    determining at least one characteristic parameter corresponding to a respiration parameter of the subject on the basis of the plurality of alternating signals,
    determining, separately from the at least one characteristic parameter, a calibration value on the basis of a breathing volume measured during at least one of an inhale and exhale of the subject by means of an airflow measurement,
    calculating the respiration volume of the subject on the basis of the calibration value and the characteristic parameter, wherein the plurality of alternating signals are weighted by a weight factor; and
    controlling a display device to continuously display the calculated respiration volume of the subject.

13. The non-transitory computer readable medium as claimed in claim 12, the method further including:
    determining the plurality of alternating signals on the basis of movement pattern derived from the image data.

14. The non-transitory computer readable medium as claimed in claim 12, the method further including:
    selecting at least one area in the field of view on the basis of the plurality of alternating signals determined from the field of view; and
    determining a frequency spectrum or spectral energy distribution of the plurality of alternating signals for selecting the at least one area.

15. The non-transitory computer readable medium as claimed in claim 13, the method further including:
   determining the characteristic parameter on the basis of the plurality of alternating signals determined from the selected area.

16. The non-transitory computer readable medium as claimed in claim 12, the method further including:
   measuring the breathing volume of the subject during at least one of the inhale and the exhale cycle.

17. The non-transitory computer readable medium as claimed in claim 12, the method further including:
   correlating the characteristic parameter and the measured breathing volume to determine the calibration value and to calculate the respiration volume.

18. The non-transitory computer readable medium as claimed in claim 12, the method further including:
   measuring the breathing volume of the subject during an inhale and an exhale cycle;
   correlating a maximum inhale volume to the corresponding maximum of the characteristic parameter;
   correlating a minimum inhale volume to the corresponding minimum of the characteristic parameter to determine the calibration value; and
   scaling the characteristic parameter according to the determined calibration value to continuously calculate the respiration volume.

19. An apparatus for determining a respiration volume signal from a human subject, the apparatus comprising:
   a camera arranged remote from the human subject and configured to acquire image data from the field of view;
   a spirometer configured to determine a calibration value on the basis of a breathing volume measured during at least one of an inhale and exhale of the subject; and
   at least one electronic processor programmed to:
      receive image data detected from the field of view from the camera;
      determine a plurality of alternating signals including vital sign information of the subject from different areas of the field of view from the image data by operations including:
         determine an energy distribution parameter of the plurality of alternating signals;
         select at least one area in the field of view based on the determined energy distribution parameter,
      determine at least one characteristic parameter corresponding to a respiration parameter of the subject on the basis of the plurality of alternating signals,
      calculate the respiration volume of the subject on the basis of the calibration value and the at least one characteristic parameter wherein the plurality of alternating signals are weighted by a weight factor;
      control a display device to continuously display the calculated respiration volume of the subject;
   wherein the spirometer is further configured to
      measure the breathing volume of the subject during an inhale and an exhale cycle;
      correlate a maximum inhale volume to the corresponding maximum of the characteristic parameter;
      correlate a minimum inhale volume to the corresponding minimum of the characteristic parameter to determine the calibration value; and
      scale the characteristic parameter according to the determined calibration value to continuously calculate the respiration volume.

* * * * *